United States Patent [19]

Padovan et al.

[11] Patent Number: 5,041,652

[45] Date of Patent: Aug. 20, 1991

[54] METHOD FOR THE PREPARATION OF A CATALYST FOR THE AMMOXIMATION OF CARBOXYLIC COMPOUND

[75] Inventors: Mario Padovan, Milan; Giordano De Alberti, Besnate; Paolo Roffia, Saronno, all of Italy

[73] Assignee: Montedipe S.P.A., Milan, Italy

[21] Appl. No.: 584,394

[22] Filed: Sep. 17, 1990

Related U.S. Application Data

[60] Continuation of Ser. No. 311,351, Feb. 15, 1989, abandoned, which is a division of Ser. No. 216,550, Jul. 8, 1988, abandoned.

[30] Foreign Application Priority Data

Jul. 14, 1987 [IT] Italy .................. 21266 A/87

[51] Int. Cl.$^5$ ............................ C07C 131/04
[52] U.S. Cl. .................... 564/267; 564/259; 564/268
[58] Field of Search .............. 564/259, 267, 268

[56] References Cited

U.S. PATENT DOCUMENTS 3,960,954  6/1976  Russell et al. .................. 564/267
4,745,221  5/1988  Roffia et al. .................... 564/267

FOREIGN PATENT DOCUMENTS 0208311  1/1987  European Pat. Off. .

*Primary Examiner*—Mukund J. Shah
*Assistant Examiner*—Jyothsna Venkat
*Attorney, Agent, or Firm*—Morgan & Finnegan

[57] ABSTRACT

The present invention relates to a method of preparing a catalyst for the ammoximation of carboxylic compounds, consisting of a synthetic, crystaline and porous material based on silicon and titanium oxides, characterized in that a preformed matrix of amorphous silica is impregnated with an aqueous solution, containing a titanium compound and an organic compound of nitrogen, as a templating agent, and that to the thus impregnated material a zeolitic structure is given by means of a hydrothermal synthesis of usual type, shape and size of the matrix being substantially maintained unchanged.

16 Claims, No Drawings

METHOD FOR THE PREPARATION OF A CATALYST FOR THE AMMOXIMATION OF CARBOXYLIC COMPOUND

This is a continuation of application Ser. No. 311,351, filed on Feb. 15, 1989 which is a division of Ser. No. 216,550, filed July 8, 1988, both now abandoned.

BACKGROUND OF THE INVENTION

The invention relates to a method of preparing a catalyst showing a zeolitic-structure, containing silicon and titanium, particularly suitable for the ammoximation of carbonylic compounds in trickle bed reactors.

It is known, from German patent No. 1,245,371, to obtain cyclohexanone-oxime by catalytic reaction in the liquid phase of cyclohexanone with ammonia and hydrogen peroxide ("ammoximation reaction"), at a temperature from 5° to 40° C. and according to suitable ratios of the reactants to each other, in the presence of a catalyst consisting of phospho-tungstic acid or similar compounds. A drawback of this method is however that this type of catalyst is difficult to handle, above all during the separation of the product from the catalyst. European patent publication 208,311 in the Applicant's name, teaches that an effective alternative can be residing in the catalysis by a synthetic, crystalline, porous material based on silicon and titanium oxides (titanium-silicalite); see also, in this connexion, U.S. Pat. No. 4,410,501 and European patent publication Nos. 132,550 and 190,609. The Applicant has also found that a special post-treatment type (with $H_2O_2$) of titanium-silicalites endows these latter with exceptional, and at all surprising catalytic properties in the reaction of ammoximation of various carbonylic compounds (see European patent application No. 87/108,577) and that the thus activated titanium-silicates can be used for continuous operations, both in an isothermal suspended-bed reactor, equipped with stirring means, and in an adiabatic trickle bed reactor. A titanium-silicalite can be prepared by starting from several titanium sources (e.g., tetra-ethyl ortho-titanate, tetra-isopropyl ortho-titanate or peroxy-titanates optionally formed in situ and so forth), and from several silicon sources (tetra-ethyl ortho-silicate, silica sol and so forth). The product, obtained downstream the hydrothermal synthesis and the subsequent thermal treatments and treatments of activation with $H_2O_2$, is microcrystalline. If the ammoximation process has to be accomplished in a trickle-bed reactor, a careful shaping of the catalyst is necessary, by resorting to further steps, such as pugging the titanium-silicalite with a suitable binding agent and then giving the mixture the shape of spheres, pellets, extrudates (optionally polylobate extrudates, having helical or non-helical grooves) and so forth. The Applicant has now developped a method allowing to obtain titanium-silicalite based catalysts, directly in sphere, pellet or extrudate shape, in an extremely simpler way.

DISCLOSURE OF THE INVENTION

In its broadest aspect, the invention relates to a method of preparing a catalyst consisting of a crystalline, porous material, based on silicon and titanium oxide, particularly suitable for the ammoximation of carbonylic compounds in trickle-bed reactors, characterized in that a preformed matrix of amorphous silica is impregnated with an aqueous solution, containing a titanium compound and an organic nitrogen compound, acting as a templating agent, and that to the thus impregnated material a zeolitic structure is given, by means of a hydrothermal synthesis of usual type, shape and size of the silica matrix being substantially preserved. The matrix of amorphous silica can be consisting of spheres, extrudates (e.g. polylobate extrudates, optionally showing helical grooves) or silica pellets, in the normally available type and size. The silicas having a surface area from 80 to 160 mq/g, a volume of the pores from 0.5 to 1.5 $cm^3/g$, in the form of extrudates having a diameter from 1 to 10 mm, preferably from 3 to 6 mm, have shown to be particularly suitable.

As a titanium source, several water-soluble compounds can be used, such as, e.g., alkyl titanates, $TiOCl_2$, peroxytitanates (optionally formed in situ), diisopropylbis-trietanolamine titanate and so forth; the Si:Ti molar ratio in the catalyst is advantageously at least 30, and preferably 50. Tetrapropylammonium hydroxide can be considered as one of the most widely used templating compounds.

Very good results were obtained by impregnating a preformed amorphous silica, dried at temperatures from 100° to 350° C., according to the dry impregnation technique, described e.g. by IND. ENG. CHEM. PROD RED. DEV., Volume 20 (1981), page 441.

The thus impregnated pre-formed and solid material is transferred to an autoclave and is kept therein at a temperature from 150° to 200° C., preferably (approximately) 175° C., and under its autogenous pressure, for a time from 2 to 20 days, preferably from 3 to 11 days. At the end of the hydrothermal synthesis, the solid material, which retains the shape and size of the silica used as the starting material, is washed with $H_2O$ up to neutral pH and is dried at 120°–130° C. for 15 hours, then optionally calcined (for instance at 430° C. for 10 hours).

Then best yields are obtained by subsequently applying an activating wash with an aqueous solution of hydrogen peroxide, optionally in the presence of an acid having a pK equal to or lower than 5, preferably selected from sulphuric, phosphoric and hydrochloric acid, or in the presence of at least 10 kg of $NH_3$ per 100 kg of solution.

The catalysts prepared according to the invention were successfully used in continuous runs, for many tens of hours, and with no traces of decay, for the ammoximation with $H_2O_2$ and $NH_3$ of various carbonylic compounds, such as e.g. acetone, cyclohexanone, methyl-ethyl-ketone (butan-2-one), acetophenone or cyclododecanone. Particularly good results are obtained when the ammoximation is preceded by an activating washing of the catalyst, as disclosed e.g. in European patent application 87/108,577. The thus obtained catalyst can be used in trickle-bed reactors, equipped with surfaces compatible with hydrogen peroxide.

The conversion to oxime can be carried out at a temperature from 25° to 100° C. (preferably from 40° to 90° C., still more preferably from 60° to 90° C.); test carried out at 15° C. gave decidedly poor results. The reaction can be carried out under atmospheric pressure, or under a slightly higher pressure, in order to keep dissolved, inside the reaction medium, at least an amount of ammonia which corresponds to the synthesis requirement. The $H_2O_2$: carbonylic compound molar ratio is generally from 0.3 to 2.5 and preferably from 0.5 to 1.5, by "$H_2O_2$" 100% pure hydrogen peroxide being meant (dilution water excluded). The $NH_3$: carbonylic compound molar ratio is equal to or larger than 1 (preferably 1.5), otherwise parallel disturbing reactions take place. The reaction medium can be consisting of water or by an organic solvent; really exceptionally good results were obtained by using as the solvent tert.butyl alcohol and/or cyclohexanol, possibly mixed with dioxane or toluene. The tert.-butanol (and/or cyclohexanol): carbonylic compound molar ratio should generally be from 0.1 to 100. Maintaining the hourly space velocity within the range from 0.1 to 200 kg/hour (preferably from 2 to 200 kg/h) of ketone per kg of pure catalyst (binding agent excluded), and feeding ketone as a mixture with the organic solvent e.g. tert.-butanol (and/or cyclohexanol), is recommended.

EXAMPLES

The following examples illustrate the invention, however in no way limiting the scope thereof.

EXAMPLE 1

Synthesis of Titanium-Silicalite in Form of Extrudates 0.6 g of tetraisopropyl ortho-titanate was hydrolysed with 10 cm$^3$ of de-ionized water under stirring and at room temperature, thus forming a white jelly suspension, to which 20 cm$^3$ of hydrogen peroxide (at 30% by weight) was added, a clear solution of orange color being thus obtained; to the colored solution 30 cm$^3$ were added of an aqueous solution of tetrapropylammonium hydroxide (at 20% by weight) and the resulting clear solution was concentrated by evaporation to a volume of 20 cm$^3$. 30 g of extrudates (solid cylinders) of 4 mm of diameter), consisting of amorphous silica, having a surface area of 120 m$^2$/g and a volume of the pores of 1.1 cm$^3$/g, were loaded into a rotary flask kept under vacuum. The above solution was slowly poured onto the extrudate, always maintaining the vacuum inside the flask. The thus impregnated extrudates were transferred to an autoclave and submitted to a hydrothermal synthesis at 175° C. for 9 days under autogenous pressure. At the end, after cooling, the obtained solid, still in the form of extrudates, was washed a long time with de-ionized water, to neutral pH, dried at 120° C. for 15 hours and then calcined at 430° C. for 10 h. The elemental analysis showed that the solid contained titanium, according to an Ti/(Ti+Si) atomic ratio=0.45%; the X-ray diffraction showed the presence of a crystalline product characterized by the typical reflections of titaniumsilicalite, such as those shown in U.S. Pat. No. 4,410,501. The presence of titanium-silicalite was confirmed by the I. R. spectrum, where the typical bands at 960 and 550 cm$^{-1}$ were present (see the U.S. patent hereinabove) and by the nitrogen absorption isotherm (BET method).

EXAMPLE 2

Catalyst Activation with H$_2$O$_2$ 13 g of the product obtained in Example 1 were poured into an aqueous solution, prepared from 26 cm$^3$ of hydrogen peroxide (at 30% by weight), and 230 cm$^3$ of diluted sulphuric acid (at 10% by weight); the resulting mixture was then stirred for 2 hours at 70° C.; the liquid was decanted off. This activation was repeated once more with a fresh solution; the extrudates were filtered off from the liquid and washed with de-ionized water (to neutral pH) The product was finally dried at 120° C. for 15 hours and calcined at 550° C. for 2 hours.

EXAMPLE 3

2 g of the catalyst obtained according to Example 1 were loaded into a trickle bed reactor, fed with 12 cm$^3$/h of an organic solution (containing 8.67% by weight of cyclohexanone, 44.53% by weight of tert.-butyl alcohol and 40.80% by weight of water), with 0.66 cm$^3$/h of hydrogen peroxide, at 34% by weight, and with 0.4 liters/h of ammonia gas; at the temperature of 80° C. a conversion of cyclohexanone of 35.5% and a corresponding selectivity to oxime of 74.8% were obtained.

EXAMPLE 4

Example 3 was repeated, the catalyst of Example 1 being replaced by the catalyst of Example 2; a conversion of cyclohexanone of 37.6%, and a corresponding selectivity of oxime of 93.6% were obtained.

EXAMPLE 5

5 g of the catalyst prepared according to Example 1 were loaded into a trickle bed reactor, fed with 30 cm$^3$/h of an organic solution (containing 8.10% by weight of cyclohexanone, 2.64% by weight of H$_2$O$_2$, 40.90% by weight of tert.-butyl alcohol and 48.36% by weight of water) and with 1 liter/h of ammonia gas; at the temperature of 80° C., a conversion of cyclohexanone of 47.5%, and a selectivity to oxime of 79.8% were obtained.

EXAMPLE 6

Example 1 was repeated, a different type of silica being submitted to impregnation, which was characterized by a surface area of 90 cm$^2$/g, and by a pore volume of 0.6 cm$^3$/g, and which was in the form of extruded cylinders having 2 mm of diameter. For the impregnation, a solution was used, which had been concentrated by evaporation to half-volume (with respect to the one of Example 1), the further portion of the impregnation procedure being kept unchanged. The formation of titanium-silicalite was confirmed by X-ray diffraction spectroscopy, I.R. spectroscopy and nitrogen absorption (BET). Also this catalyst proved to be suitable for the reaction of ammoximation of carbonylic compounds in a trickle-bed reactor, yielding high selectivities to oxime.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A method for the ammoximation of a carbonylic compound, selected from acetone, methyl-ethyl-ketone, cyclohexanone, cyclododecanone and acetophenone, in the presence of a catalyst consisting essentially of a synthetic crystalline porous zeolitic material, based on silicone and titanium oxides, prepared from silica, as the source of silicon, by impregnating said silica with an aqueous solution, containing a titanium compound and an organic nitrogen templating agent, and by submitting the thus-impregnated silica to a hydrothermal synthesis, the improvement residing in that said silica is an amorphous silica consisting of preformed extruded granules.

2. The method of claim 1, wherein said extruded granules are extruded pellets.

3. A method according to claim 1, wherein said impregnation is a dry-impregnation.

4. A method according to claims 1 or 3, wherein said extruded granules have a polylobate shape.

5. A method according to claim 4, wherein the polylobate shape includes helical grooves.

6. A method according to claim 1 or 3, wherein said hydrothemal synthesis is followed by a subsequent thermal treatment at a temperature equal to or lower than 430° C., and by a subsequent activating washing with an aqueous solution of hydrogen peroxide.

7. A method according to claim 6, wherein the subsequent thermal treatment is carried out at a temperature of about 130° C.

8. A method according to claim 6, wherein said washing takes place in the presence of an acid having a pK equal to or lower than 5.

9. A method according to claim 8, in the presence of an acid selected from the group consisting of sulphuric, phosphoric and hydrochloric acids.

10. A method according to claim 6, wherein said aqueous solution of $H_2O_2$ contains at least 10 kg of $NH_3$ per 100 kg of solution.

11. A method according to claim 1 or 3, wherein the ratio of the source of silica to the source of titanium is such that the Si:Ti molar ratio, in the finished catalyst, is equal to or greater than 30.

12. A method according to claim 11, wherein the said Si:Ti molar ratio is 50.

13. A method according to claim 1 or 3, wherein the titanium compound used as the starting material is selected from the class consisting of alkyl-titanates and peroxy-titanates.

14. A method according to claim 13, wherein the titanium compound used as the starting material is formed in situ.

15. A method according to claim 1 or 3, wherein the ammoximation is carried out continuously while the said catalyst is disposed inside a trickle-bed reactor.

16. A method for the ammoximation of a carbonylic compound selected from the group consisting of acetone, methyl-ethyl-ketone, cyclohexanone, cyclododecanone and acetophenone, in the presence of a catalyst consisting essentially of a synthetic crystalline porous zeolitic material based on silicon and titanium oxides, wherein the source of the silicon is silica, comprising impregnating said silica with an aqueous solution containing a titanium compound and an organic nitrogen templating agent to prepare said catalyst; and submitting the thus-impregnated silica to a hydrothermal synthesis; wherein said silica is an amorphous silica consisting essentially of extruded granules.

* * * * *